United States Patent [19]

Serwer et al.

[11] Patent Number: 5,162,514

[45] Date of Patent: Nov. 10, 1992

[54] HIGH MOLECULAR WEIGHT DNA COMPOSITIONS FOR USE IN ELECTROPHORESIS OF LARGE NUCLEIC ACIDS

[75] Inventors: Philip Serwer; Donna F. Louie, both of San Antonio, Tex.

[73] Assignee: Board of Regents, University of Texas, Austin, Tex.

[21] Appl. No.: 523,766

[22] Filed: May 15, 1990

[51] Int. Cl.$^5$ .................. C07H 17/00; C12P 19/36
[52] U.S. Cl. .......................... 536/27; 435/91
[58] Field of Search ................ 536/27; 435/91

[56] References Cited

U.S. PATENT DOCUMENTS 4,473,452 10/1984 Cantor et al. .................. 204/182
4,710,465 7/1987 Weissman et al. ............... 435/91

OTHER PUBLICATIONS

Carle et al., "Separation of Chromosomal DNA Molecules from Yeast by Orthogonal-Field-Alternation Gel Electrophoresis", *Nucleic Acids Research*, 12(14):5647-5664 (1984).

Mathew et al., "High-Resolution Separation and Accurate Size Determination In Pulsed-Field Gel Electrophoresis of DNA. 1. DNA Size Standards and the Effect of Agarose and Temperature", *Biochemistry*, 27(26):9204-9210 (1988).

Hanlon et al., "Plasmid Multimers As High Resolution Molecular Weight Standards for Pulsed Field Gel Electrophoresis", *Nucleic Acids Research*, 17(13):5413 (1989).

Ritchie, D. A. et al., *J. Mol. Bio.* 23:365-376 (1967).
Kelly, T. J., Jr. and Thomas, C. A., Jr., *J. Mol. Biol.* 44:459-475 (1969).
Kerr, C. and Sadowski, P. D., *Proc. Nat. Acad. Sci. USA* 71:3545-3549 (1974).
Sadowski, P., et al., *Can. J. Biochem.* 52:525-535 (1974).
Miller, R. C., Jr., et al., *J. Mol. Biol.* 101:223-234 (1976).
Fangman, W., *Nuc. Acids Res.* 5:653-665 (1978).
Kuemmerle, N. B. and Masker, W. E., *J. Virol.* 23:509-516 (1977).

Sadowski, P. D., *Birol.* 78:192-202 (1977).
Langman, L., et al., *Can. J. Biochem* 56:508-516 (1978).
Masker, W. E., et al., *J. Virol.* 27:149-163 (1978).
Rosenberg, A. H., et al., *J. Mol. Biol.* 135:907-915 (1979).
Fujisawa, H. et al., *Virol.* 101:327-334 (1980).
Fujisawa, H. et al., *Virol.* 105:480-489 (1980).
Yamagishi, M., et al., *Virol.* 100:382-389 (1980).
Serwer, P., *Biochemistry* 19:3001-3004 (1980).
Serwer, P., and Greenhaw, G. A., *Electrophoresis* (1981).
Serwer, P. and Watson, R. H., *Virol.* 198:164-176 (1981).
Dunn, J. J. and Studier, F. W., *J. Mol. Biol.* 166:477-535 (1983).
Furth, M. E. and Wickner, S. H., *Lambda II*, pp. 145-173 (1983).
Serwer, P., et al., *J. Virol.* 45:665-671 (1983).
Studier, F. W. and Dunn, J. J., Cold Spring Harbor Symposia on Quantitative Biology, vol. XLVII, pp. 999-1007 (1983).
Cajens, S. (Ed.) *Virus Structure and Assembly*, pp. 76-147 (1985).
Lee, D. D. and Sadowski, P. D., *Can. J. Biochem. Cell Biol.* 63:237-242 (1985).
Anand, R., *Trends Gen.* 2:278-283 (1986).
Hamada, K., et al., *Virol.* 151:119-123 (1986).
Serwer, P. and Hayes, S. J., *Electrophoresis* 8:244-246 (1987).
Serwer, P., et al., *J. Virol.* 61:3499-3509 (1987).
Serwer P., *Electrophoresis* 8:301-304 (1987).
Shibata, H., et al., *J. Mol. Biol.* 196:845-851 (1987).
Son, M. and Serwer, P., *Abstract Proc. Am. Soc. Biol. Chemists* (1987).
White, J. H. and Richardson, C. C., *J. Biol. Chem.* 262:8851-8860 (1987).
White, J. H. and Richardson, C. C., *J. Biol. Chem.* 262:8845-8850 (1987).
Son, M., et al., *Virol.* 162:38-46 (1988).
Watson, J. D., et al., *Molecular biology of the Gene*, vol. 1, 4th Ed., pp. 298-299, 503-548 (1987).
DNASTAR, Product Announcement Memorandum (1988).
FMC BioProducts, Product Announcement Memorandum (1988).

Calenda, R. (Ed.) *The Bacteriophages*, vol. 1, pp. 259–289, 439–475 (date of publ. unknown).
Serwer, P. and Hayes, S. J. (in press), *Appl. Theor. Electrophoresis*
Dialog Search.
Reive et al.
Hayaski et al., *Nucleic Acids Research* 14(19):76177631 (1986).
Takahaski and Uchida, *J. Biochem.* 100:123–131 (1986).
Rusche and Howard-Flanders, *Nucleic Acids Research* 13(6):1997–2008 (1985).
Zimmerman and Harrison, *Nucleic Acids Research* 13(7):2241–2249 (1985).
Hayaski et al., *Nucleic Acids Research* 13(2):7979–7992 (1985).
Hayaski et al., *Nucleic Acids Research* 13(9):3261–3271 (1985).
Harrison and Zimmerman, *Nucleic Acids Research* 12(21):8235–8251 (1984).
Zimmerman and Pheiffer, *Proc. Natl. Acad. Sci. USA* 80:5852–5856 (1983).
Pheiffer and Zimmerman, *Nucleic Acids Research* 11(22):7853–7871 (1983).
Ferretti and Sgaramella, *Nucleic Acids Research* 9(15):3695–3705 (1981).
Dialog Accession Number 5401935.
Dialog Accession Number 4630759.
Dialog Accession Number 3494983.

*Primary Examiner*—John W. Rollins
*Attorney, Agent, or Firm*—Arnold, White & Durkee

[57] ABSTRACT

The invention provides high molecular weight DNA length standards useful for sizing very long DNA molecules and methods for producing such standards. In a preferred embodiment, the invention provides a mixture of T4 DNA concatemers that forms a DNA "ladder" having rungs differing by at least 0.17 Mb (Megabases) in length upon gel electrophoresis and methods for producing and using such compositions.

11 Claims, 1 Drawing Sheet

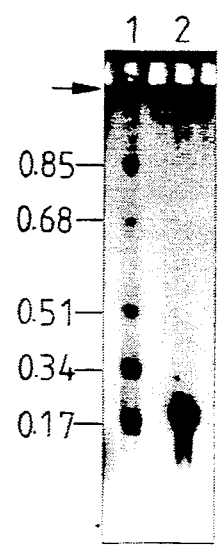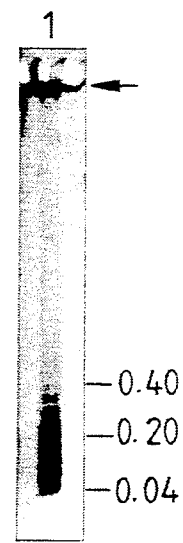
FIG.1a  FIG.1b

HIGH MOLECULAR WEIGHT DNA COMPOSITIONS FOR USE IN ELECTROPHORESIS OF LARGE NUCLEIC ACIDS

FUNDING: Development of the present invention was aided in part by funding from The National Institutes of Health (Grant no. GM24365). Accordingly, the Federal Government may own certain rights. Development of the invention was also facilitated by funding from the Texas Coord. Board (Grant No. 004).

FIELD OF THE INVENTION

The present invention provides high molecular weight DNA length standards useful for sizing very long DNA molecules and methods for producing such standards. In a preferred embodiment, the invention provides a mixture of T4 DNA concatemers (end-to-end multimers of the monomeric DNA) that forms a DNA "ladder" having rungs differing by at least 0.17 Megabases (Mb) in length upon gel electrophoresis and methods for producing and using such compositions. Also included are compositions containing pentameric or hexameric concatemers of T4 DNA and methods for blunt-end ligation of DNA to produce extremely long (e.g. 1 Mb) DNA molecules.

DESCRIPTION OF THE RELATED ART

As the study of molecular biology has evolved, workers in the field have strived to manipulate and fractionate by size larger and larger pieces of DNA, using the molecular tools previously successful with smaller DNA fragments. However, serious difficulties arise when manipulating very large DNA molecules. Recent advances in the field of electrophoresis utilize rotating gels or pulsing electric fields. Fortunately, using these new techniques, it is now possible to fractionate by length DNA molecules as long as 10 Mb (Cantor, et al., 1988; Cantor and Schwartz, 1984; Serwer, 1987; U.S. Pat. No. 5,041,203 incorporated herein by reference).

One of the major problems remaining for workers wishing to use the new techniques is the lack of stable, reproducible, discrete length standards. The most useful primary length standards used in the past have been obtained by annealing single-stranded cohesive ends of mature, 49 Kilobase (kb) bacteriophage $\lambda$ DNA to form concatemers that produce a series of bands or "ladder" during electrophoresis.

Unfortunately, the relatively short size of the $\lambda$ DNA makes it poorly suited for use as standards in sizing very long ($\geq 1.5$ Mb) DNAs. Further, concatermerization of $\lambda$ DNA requires 12 bp cohesive terminal repeats which may be damaged before or during the concatemerization process, thereby further limiting the length of the concatemers. The $\lambda$ concatemers that do form are not particularly stable to denaturation since the overlapping ends are quite short. Thus, when used under conditions that even mildly denature DNA, such as elevated temperature, bacteriophage $\lambda$ standards are destabilized and rendered useless as DNA length markers.

Additional problems arise with the $\lambda$ standards if the standard preparation is allowed to sit for even short periods of time. Since the concatemerization is non-enzymatic, the preparations tend to further concatemerize over time giving rise to non-reproducible results from one usage to the next and to a much shorter shelf life.

An improved DNA sizing ladder, obtainable by a process employing enzymatic concatemerization of the so called "T-odd" bacteriophage (particularly T7) DNA (40 kb), was described in U.S. Pat. No. 5,030,566 and incorporated herein by reference. However, that method involved use of a relatively complex mixture, involving cellular enzymes and extracts and the like. Thus, although the methods represented a great advance in the art, significant room for improvement remained, and compositions of DNA for sizing very long DNA molecules continued to be sought.

SUMMARY OF THE INVENTION

Fortunately, the present inventors have now discovered a convenient, reproducible technique for generating stable DNA compositions suitable for sizing very long DNA molecules. The technique has allowed production of DNA "ladders" having rungs spaced by more than 0.05 Mb, and has even allowed production of ladders with at least 6 rungs spaced by up to 0.17 Mb. The method has been successfully employed to join blunt ended segments of DNA to produce very long molecules (greater than about 1 Mb).

One embodiment of the invention includes a composition of matter comprising a first DNA species of about 1x Mb in length, a second DNA species of about 2x Mb in length, and a third DNA species of about 3x Mb in length. In this embodiment, x is a constant greater than about 0.05. When subjected to gel electrophoresis, the composition is capable of generating a series of discrete bands, the DNA within any one of such bands differing in length from the DNA of any other one of such bands by an integral multiple of x. In yet a further embodiment, a composition of matter is provided that consists essentially of a first DNA species of about x Mb in length, a second DNA species of about 2x Mb in length, and a third DNA species of about 3x Mb in length, wherein x is a constant greater than about 0.05, and more preferably, is at least about 0.17.

Also included is a composition of matter comprising a mixture of monomers and oligomers of a selected DNA molecule. In this embodiment the monomers of the molecule are at least about x Mb in length. Preferably, x is greater than about 0.05 Mb, and more preferably x is about 0.17. Further, the mixture is characterized in that, upon electrophoresis under suitable conditions, the DNA migrates to form discrete bands of DNA, each band containing a species of DNA of about n(x) Mb in length, wherein n is an integer. Preferably, the monomer DNA species will be a "blunt ended" species. In a more preferred embodiment the oligomers will comprise dimers, and trimers, and more preferably, tetramers. In an even more highly preferred embodiment, the oligomers will comprise pentamers, or even more preferably, hexamers. In yet a further embodiment, the selected DNA molecule of the composition is a T4 bacteriophage DNA of about 0.17 Mb in length (as a monomer).

The invention also includes a number of novel methods for preparation of the compositions. For example, the invention includes a method for preparing a mixture of monomers and oligomers suitable for use as DNA size standards comprising the following steps: obtaining a purified preparation of a selected DNA molecule of at least about x Mb in length (wherein x is a constant greater than about 0.05), mixing the preparation with a ligase and polyethylene glycol under conditions suitable to allow a concatemerization reaction to occur; and terminating the concatemerization reaction to obtain a stable mixture comprising the DNA molecules and concatemers thereof. In an embodiment that is more highly preferred, termination of the concatemerization produces a stable mixture containing concatemers of the DNA molecules, characterized in that, upon electrophoresis under suitable conditions, the DNA molecules migrate to form a series of discrete bands of DNA, the DNA in each band differing in length from the DNA in any other band by about n(x) Mb, wherein n is an integer. Preferably, the DNA molecules are blunt ended, and more preferably T4 molecules and x is about 0.17. T4 ligase is most advantageously used. The polyethylene glycol will generally comprise a polyethylene glycol of high molecular weight, for example, at least about 3000, and most preferably at least about 6000.

The invention also includes a method for joining large blunt-ended pieces of DNA to produce ligated DNA molecules of at least about 1 Mb in length. Such ligated molecules are advantageous in both size and stability. Unlike molecules joined by complementary base pairing of so-called "cohesive ends," blunt end ligated molecules are not subject to depolymerization under conditions (such as increased temperature or changes in salt concentration) which can cause the cohesive ends to "melt" or come apart. According to the invention, therefore, there is provided a method for blunt end ligation of DNA which comprises the steps of obtaining a preparation of blunt ended DNA molecules; incubating the preparation together with a ligase and polyethylene glycol under conditions suitable for ligation of the blunt ended DNA molecules; and terminating the ligation reaction to obtain a preparation comprising DNA molecules of at least 1 Mb in length.

Although certain of the reaction conditions for concatemerization may be varied, the present inventors have discovered a unique set of reaction conditions that are exceedingly and surprisingly satisfactory. The invention includes a method wherein the concatemerization conditions comprise about 20 μg/ml DNA, more preferably about 18.75 μg/ml; about 10% (w/w) polyethylene glycol 6000 or more preferably 9.5% (w/w); about 70 mM NaCl, more preferably 67.5 mM; about 7 mM NaPO$_4$, pH 7.4, more preferably, 6.75 mM; about 0.7 mM EDTA, pH 7.4, more preferably 0.675 mM; in a buffer comprising about 50 mM Tris-Cl, pH 7.4 about 10 mM MgCl$_2$, about 20 mM dithiothreitol, about 1 mM ATP, and about 50 μg/ml bovine serum albumin. Preferably, the termination step will be performed after between about 5 hours and about 10 hours of incubation, and most preferably after about 6 hours of incubation. Also preferred is a method wherein the termination step comprises inactivating the ligase by heating, for example, at about 75° C. for about 15 minutes.

Using these methods, the present inventors have achieved ladders of DNA with rungs many times further apart than ever before achieved. Accordingly, the present invention also includes a T4 DNA concatemer of at least about 1 Mb in length, and a pentamer or a hexamer of a 0.17 Mb T4 DNA molecule.

These and other aspects of the invention will become more apparent from a description of particular embodiments when read in conjunction with the drawings.

DESCRIPTION OF THE DRAWINGS

FIG. 1: Panel (a) depicts T4 DNA ladders; Panel (b) depicts T7 DNA ladders. The gels were stained with ethidium bromide. The length of DNA in Mb is indicated.

DESCRIPTION OF A PREFERRED EMBODIMENT

In a general and overall sense, the present invention includes the steps of preparing a concatemer (or oligomer) of a selected DNA monomer, where the selected monomer comprises more than about 0.05 Mb. Although a number of suitably long DNA monomers may be successfully employed with the aid of this disclosure, preferably, the monomer will comprise a long blunt ended segment of DNA such as mature T4 DNA or DNA from bacteriophage G or T5 (0.12 Mb). Although the DNA will usually be double stranded, when the standard is desired for use in sizing a single stranded DNA preparation, use of a single stranded concatemer may be preferred. The DNA may be extracted from the bacteriophage by any of a number of suitable methods, for example, those described below in example I, taking care to avoid unnecessary breakage of the DNA molecules during the isolation procedure. The invention also provides a method whereby long segments of blunt ended DNA can be ligated to produce very long (1 Mb or more) DNA molecules.

For the reaction, the DNA is incubated in a suitable incubation mixture for between about 3-6 hours, and most preferably about 6 hours. Generally, the mixture will contain a high molecular weight polyethylene glycol such as polyethylene glycol 4000, 6000, or 12500, a DNA ligase (preferably T4 ligase), and a suitable reaction buffer. Most commonly, the PEG concentration will comprise about 10% by weight of the final ligation mixture. Although incubation at 37° C. is preferred, the incubation step may also be conducted at room temperature. After incubation, the concatemerization reaction is terminated by an inactivation of the ligase, preferably by heating, e.g., at about 75° C. for 15 minutes. Less satisfactory results are obtained when one uses 0.01M EDTA to stop the reaction.

These and other aspects of the invention will become more apparent when read in context of the examples below. The examples are not intended to limit the scope of the claims unless so specified in the claims therein.

A. Preparation of Bacteriophage Stock

A preparation of T4 bacteriophage was added to a lawn of log phase *E. Coli* BB/1 on T broth plates. The plates were incubated at 30° C. for approximately 24–30 hours to allow formation of plaques. A plate containing approximately 25–100 plaques was selected, a single isolated plaque was selected, and a plug of agar containing the plaque (bacteriophage plug) was removed from the plate, and transferred to sterile T7 buffer (0.5M NaCl, 0.01M Tris-Cl, pH 7.4, 0.001M MgCl$_2$, 1 mg/ml gelatin) containing a few drops of chloroform. The bacteriophage plug was stored in this solution at 4° C. for up to approximately one week.

In the next step of the procedure, a log phase culture of BB/1 was grown to a density of approximately 1×10$^8$ cells per ml in 2×LB (Luria-Bertani) medium. Then, a bacteriophage plug, prepared as described above, was added to 100 ml of the BB/1 culture. After incubation with the bacteriophage for about four hours, the bacteria were lysed by addition of chloroform. For that procedure, several drops of chloroform were bubbled into the mixture until the bacteria lysed. At the same time that the chloroform was added, NaCl was added to a final concentration of 1M. Bacterial debris was removed by centrifugation at 7000 RPM for 7 minutes. After centrifugation, the supernatant, which contained the T4 bacteriophage, was removed. The titer of the bacteriophage stock was determined by plating the bacteriophage on a lawn of E. Coli BB/1.

The titered bacteriophage stock was used in a subsequent large scale infection to produce T4 bacteriophage from which T4 DNA was obtained. For that procedure, an isolated colony of E. Coli BB/1 was inoculated into a 50 ml flask of medium M9. After overnight incubation, a 25 ml aliquot of the initial preparation was added to 6 liters of M9 medium and the mixture was cultured to a bacterial cell density of $3 \times 10^8$ cells per ml. The bacteria were infected with T4 bacteriophage at a multiplicity of infection of $10^{-3}$, and the mixture was incubated for about 3 hours. Then, the culture was brought to 0.5M sodium chloride, 22 ml of chloroform, and 8-10% polyethylene glycol 6000 was added to the preparation. The mixture was maintained at 4° C. for about 2-7 days. Then, the mixture was centrifuged at 4° C. for 45 min at 4000 RPM to pellet the bacteriophage. The sedimented material, i.e., the bacteriophage, was resuspended in approximately 130 ml of sterile T7 buffer without gelatin, carbowax was added to 9%, and the mixture was incubated at 4° C. overnight. The material was centrifuged at 5000 RPM for 10 min, the pellet was resuspended in 5.5 ml T7 buffer without gelatin containing a final concentration of 2.5 µg/ml DNAse I and incubated at 30° C. for one hour.

A cesium chloride (0.01M Tris-Cl, pH 7.4, 0.001M. MgCl$_2$) step gradient was prepared as follows:

|  | $\eta^{25}$ | Vol. |  |
|---|---|---|---|
| Top | 1.3550 | 1.5 ml | $\eta$ - refractive index |
|  | 1.3610 | 1.0 ml |  |
|  | 1.3760 | 1.5 ml |  |
|  | 1.3820 | 1.0 ml |  |
| Bottom | 1.4020 | 1.0 ml |  |

The bacteriophage was purified further by centrifugation over the cesium chloride step gradient at 18° C. for three hours using an SW41 rotor and a speed of 33,000 RPM. After centrifugation, the bacteriophage were compressed into a visible band, which sedimented at a refractive index of about 1.3810. The band was removed from the tube and adjusted to a refractive index of 1.3810 in cesium chloride 0.01M Tris-Cl, pH 7.4, 0.001M MgCl$_2$. Then, the suspension was centrifuged on a cesium chloride buoyant density gradient at 40,000 rpm for 20 hours at 10° C. in an SW50.1 rotor, and the bacteriophage-containing band was collected as before. The cesium chloride was removed from the bacteriophage suspension by successive dialysis through a series of buffers containing decreasing salt concentrations as follows:

| NaCl | Tris-Cl (pH 7.4) | MgCl$_2$ |
|---|---|---|
| 2.5M | 0.01M | 0.001M |
| 2.0M | 0.01M | 0.001M |
| 1.25M | 0.01M | 0.001M |
| 1.0M | 0.01M | 0.001M |
| 0.05M | 0.01M | 0.001M |
| 0.1M | 0.01M | 0.001M |
| 0.2M | 0.01M | 0.001M |

Phenol Extraction of DNA

T4 DNA was then purified from the bacteriophage preparation by phenol extraction. For that procedure, T4 bacteriophage was diluted in TE buffer (0.01M Tris-Cl, pH 7.4, 0.001M EDTA) to an OD$_{260}$ of approximately 50. A 150 microliter aliquot of the diluted bacteriophage was added to an equal volume of phenol equilibrated in TE buffer in a 1.5 ml conical microfuge tube and mixed by gently inverting the tube for about 100 seconds. After that time, the mixture was centrifuged for 5 minutes in a microfuge at room temperature. The upper aqueous layer of the supernatant was transferred to a new 1.5 ml tube, an equal volume of phenol was added, and the mixture was mixed by gently inverting the tube for approximately 100 seconds. The centrifugation step was repeated, and the upper aqueous layer was removed and mixed with an equal volume of 1:1 phenol:chloroform:isoamyl alcohol (24:1). The mixture was centrifuged for 5 minutes in a microfuge at room temperature. The upper aqueous layer of the resultant supernatant was removed and dialyzed against sterile buffer (0.1M NaCl, 0.01M Tris-Cl, pH 7.4 and 0.001M EDTA) with stirring and three changes at 4° C. overnight. After dialysis, the DNA concentration was measured by a spectrophotometer at OD$_{260}$ and stored at 4° C.

Concatemerization and Electrophoresis

The T4 DNA prepared above comprised blunt-ended double stranded DNA monomers of about 0.17 Kb in length. The DNA monomers were concatemerized to form oligomers capable of forming a DNA ladder with 0.17 Mb rungs on electrophoresis as follows: Three µl of 250 µg/ml DNA were added to a mixture containing: (a) 27 µl of 14% (w/w) polyethylene glycol (PEG) 6000 in 0.1M sodium chloride, 0.01M sodium phosphate, pH 7.4, 0.001M EDTA, (b) 8 µl of 0.25M Tris-Cl, pH 7.4, 0.05M MgCl$_2$, 0.1M dithiothreitol (DTT), 0.005M ATP, 250 µg/ml bovine serum albumin (BSA), and (c) 1 µl of 3.3 units/µl T4 ligase (U.S. Biochemicals). Thus, the final concentration of reagents in the mixture was as follows: 18.75 µg/ml DNA; 9.5% PEG 6000, 67.5 mM NaCl, 6.75 mM NaPO$_4$; 0.675 mM EDTA. The ligation buffer contains 50 mM Tris-Cl, pH 7.4, 10 mM MgCl$_2$; 20 mM DTT, 1 mM ATP and 50 µg/ml BSA.

After incubation at 37° C. for 6 hr, the ligase was inactivated by incubation at 75° C. for 15 min to terminate the concatemerization reaction. Twenty-five µl of the ligation mixture (469 ng) was loaded into a well of 1% Seakem LE agarose gel cast in 0.01M sodium phosphate, pH 7.4 and 0.001M EDTA. The gel was placed in a rotating gel electrophoresis apparatus (see U.S. patent application Ser. No. 393,084, which is expressly incorporated herein by reference) and was subjected to electrophoresis at a pulse time of 120 seconds and an angle of rotation at 1.4π radians. A DNA ladder with 0.17 Mb rungs was observed. The length of the ladder appeared to be limited by the amount of broken DNA in the ligation mixture. (FIG. 1a, lane 1). The T4 ladder was not formed when the PEG was omitted (FIG. 1a, lane 2). When the ligation of FIG. 1a, lane 1 was performed using the conditions described above by use of 0.04 Mb T7 DNA, and a 11-12 rung ladder was observed (FIG. 1b).

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

What is claimed is:

1. A process for preparing a mixture of monomers and oligomers suitable for use as a DNA size standard comprising:
   (a) obtaining a purified preparation of a selected DNA molecule of at least about 0.05 Mb in length;
   (b) mixing the preparation with a ligase and polyethylene glycol under conditions suitable to allow a concatemerization reaction to occur; and
   (c) terminating the concatemerization reaction to obtain a stable mixture comprising the DNA molecules and oligomers thereof.

2. A process for preparing a mixture of DNA molecules suitable for use as a size standards for gel electrophoresis comprising the steps of:
   (a) obtaining a preparation of DNA molecules of a length x, wherein x is a constant greater than about 0.05 Mb;
   (b) incubating the preparation together with a ligase and polyethylene glycol under conditions suitable for concatemerization of the molecules to occur;
   (c) terminating the concatemerization reaction to produce a stable mixture containing oligomers of the DNA molecules, the mixture characterized in that upon electrophoresis under suitable conditions, the DNA molecules migrate to form a series of discrete bands of DNA, the DNA in each band differing in length from the DNA in any other band by about x MB.

3. A process for preparing a mixture of DNA molecules suitable for use as a size standards for gel electrophoresis comprising the steps of:
   (a) obtaining a preparation of DNA molecules of a length x, wherein x is a constant of at least about 0.17 Mb;
   (b) incubating the preparation together with a ligase and polyethylene glycol under conditions suitable for concatemerization of the molecules to occur;
   (c) terminating the concatemerization reaction to produce a stable mixture containing oligomers of the DNA molecules, the mixture characterized in that upon electrophoresis under suitable conditions, the DNA molecules migrate to form a series of discrete bands of DNA, the DNA in each band differing in length from the DNA in any other band by about x Mb.

4. The process of claim 2 wherein the DNA molecules are T4 DNA molecules and x is 0.17.

5. The process of claim 2 or claim 3 wherein the ligase is T4 ligase.

6. The process of claim 2 or claim 3 wherein the polyethylene glycol has a molecular weight greater than about 3000.

7. The process of claim 2 or claim 3 wherein the concatermerization conditions comprise:
   a) about 20 µg/ml DNA;
   b) about 10% polyethylene glycol 6000;
   c) about 70 mM Nacl ;
   d) about 7 mM NaPO$_4$;
   e) about 0.7 mM EDTA;
   in a buffer comprising about 50 mM Tris-Cl , pH 7.4, about 10 mM Mgcl$_2$; about 20 mM dithiothreitol, about 1 mM ATP, and about 50 µg/ml bovine serum albumin.

8. The process of claim 2 or claim 3 wherein the termination step occurs after between about 5 hours and about 10 hours of incubation.

9. The process of claim 2 or claim 3 wherein the termination occurs after about 6 hours of incubation.

10. The process of claim 2 or claim 3 wherein the termination step comprises inactivating the ligase by heating.

11. The process of claim 2 or claim 3 wherein the termination step comprises heating the incubated preparation at 75° C. for about 15 minutes.

* * * * *

UNITED STATES PATENT AND TRADEMARK OFFICE
CERTIFICATE OF CORRECTION

PATENT NO. : 5,162,514
DATED : November 10, 1992
INVENTOR(S) : Server, et al

It is certified that error appears in the above-indentified patent and that said Letters Patent is hereby corrected as shown below:

Column 7, claim 2, ln. 34, replace "MB" with -- Mb --.

Column 1, ln. 52, replace the symbol $\geq$ with -- $\geq$ --.

Signed and Sealed this

Second Day of November, 1993

Attest:

BRUCE LEHMAN

Attesting Officer  Commissioner of Patents and Trademarks